US00PP20011P2

(12) United States Plant Patent
Evers

(10) Patent No.: US PP20,011 P2
(45) Date of Patent: May 19, 2009

(54) GROUNDCOVER ROSE PLANT NAMED 'TAN04999'

(50) Latin Name: *Rosa L.*
Varietal Denomination: TAN04999

(75) Inventor: Christian Evers, Uetersen (DE)

(73) Assignee: Rosen Tantau, Uetersen (DE)

( * ) Notice: Subject to any disclaimer, the term of this patent is extended or adjusted under 35 U.S.C. 154(b) by 0 days.

(21) Appl. No.: 12/001,927

(22) Filed: Dec. 12, 2007

(51) Int. Cl.
*A01H 5/00* (2006.01)

(52) U.S. Cl. ..... Plt./107

(58) Field of Classification Search ..... Plt./107, Plt./108

See application file for complete search history.

*Primary Examiner*—Kent L Bell
(74) *Attorney, Agent, or Firm*—Klarquist Sparkman, LLP

(57) ABSTRACT

Groundcover rose plant having resistance to black spot, resistance to powdery mildew and prolific pink-red blooms.

3 Drawing Sheets

Genus and species: *Rosa L.*
Varietal denomination: 'TAN04999'.

SUMMARY OF THE INVENTION

The present invention relates to a new and distinct variety of ground cover rose plant named 'TAN04999', which was originated by me by crossing 'TANotax' (PP11,572, seed parent) with 'Royal Bassino' (unpatented, pollen parent).

BACKGROUND OF THE INVENTION

The primary objective of this breeding was to produce a new groundcover rose variety that is resistant to black spot and powdery mildew.

BRIEF SUMMARY OF THE INVENTION

The objective was substantially achieved, along with other desirable improvements, as evidenced by the unique combination of characteristics described hereinafter that are outstanding in the new variety and that distinguish it from its parents, as well as from all other varieties of which I am aware.

1. Resistance to black spot.
2. Resistance to powdery mildew.
3. Prolific pink-red blooms.

Asexual reproduction of this new variety by grafting on *Rosa canina* rootstock at the facilities of Rosen Tantau, Uetersen, Germany, shows that the foregoing and all other characteristics and distinctions come true to form and are established and transmitted through succeeding propagations.

COMPARISON WITH PARENTS

'TAN04999' has flowers that are darker in color than the flowers of the seed parent and the plant height is taller (60–70 cm for 'TAN04999') than its pollen parent (50–60 cm for 'Royal Bassino').

COMPARISON WITH SIMILAR VARIETY

The variety that is most similar to 'TAN04999' is believed to be 'TANotax'; as compared above.

BRIEF DESCRIPTION OF THE ILLUSTRATIONS

The accompanying illustrations show typical specimens of the flowers of this new variety depicted in color as nearly true as it is reasonably possible to make the same in color illustrations of this character.

DETAILED BOTANICAL DESCRIPTION

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—'TANotax' (PP11,572).
*Pollen parent.*—'Royal Bassino' (unpatented).

FLOWER

Observations made from plants of three years of age grown in a garden environment in Uetersen, Germany.

Blooming habit: Continuous.
Bud:
*Size.*—About 2.5 cm long and 1.6 cm in diameter when the petals start to unfurl.
*Form.*—The bud form is long.
*Color.*—When sepals first divide, bud color is Pink-Red (RHS 50A). When half blown, the upper sides of the petals are Pink-Red (RHS 511B); and the lower sides of the petals are Pink-Red (RHS 51B).
*Sepals.*—Color: Green (RHS 146B). Upper surface: Smooth. Lower surface: Hairy. Length: 2.7 cm. Width: 0.4 cm. Shape: Elongate. Surface texture: See above. There are three normally appendaged sepals. There are two unappendaged sepals with smooth edges.
*Receptacle.*—Color: Green (RHS 143B). Shape: Funnel. Size: Small, about 0.8 cm×0.4 cm. Surface: Smooth.

*Peduncle.*—Length: Medium, averaging about 1.9 cm. Surface: Smooth. Color: Green (RHS 143B). Form: Erect.

Bloom:

*Size.*—Small. Average open diameter is about 6.3 cm.

*Borne.*—Singly.

*Stems.*—Strength: Normal. Average length is about 35 cm and diameter about 0.4 cm.

*Form.*—When first open: Bloom is cupped. Permanence: Flattens and outer petal edges curl slightly.

*Petalage.*—Number of petals under normal conditions: 5.

*Color.*—The upper sides of the petals are Pink-Red (RHS 152A). The reverse sides of the petals are Pink-Red (RHS 152A). The major color on the upper side is Pink-Red (RHS 152A).

*Variegations.*—None.

*Discoloration.*—Under normal conditions no discoloration or fading.

*Fragrance.*—None.

Petals:

*Thickness.*—Thin.

*Size.*—Width 3.5 cm; Length 2.8 cm.

*Shape.*—Round.

*Margin.*—Smooth.

*Apex Shape.*—Rounded.

*Base shape.*—Rounded.

*Form.*—Edges slightly quilled.

*Arrangement.*—Regularly arranged.

*Petaloids.*—Number: 1. Color: Pink-Red (RHS 152A).

*Persistence.*—Petals drop off cleanly before drying.

*Lastingness.*—On the plant: Very long. As a cut flower: Short, (about 2 days).

Reproductive parts:

*Stamens.*—Number: 137. Length: 0.6 cm.

*Anthers.*—Length: 0.1 cm. Color: Yellow-Orange (RHS 22A). Arrangement: Regular around styles.

*Filaments.*—Color: Yellow (RHS 18C). Length: 0.5 cm.

*Pollen.*—Color: Orange (RHS 24C).

*Pistils.*—Number: 28. Length: 0.4 cm.

*Styles.*—Color: Orange (RHS 27D). Length: 0.3 cm.

*Stigmas.*—Color: Yellow (RHS 11A). Length: 0.1 cm.

*Hips.*—Color: Red. Shape: Globular. Size: Medium, 0.9 cm.

PLANT

*Form.*—Bush.

*Growth.*—Medium.

*Age to maturity.*—Approximately 5 years.

*Mature plant.*—Height: 60 cm. to 70 cm. Width: 60 cm.

*Rootstock.*—*Rosa canina.*

Foliage: Number of leaflets on normal mid-stem leaves: 5.

*Size.*—Medium, about 10.3 cm long×6.9 cm wide.

*Quantity.*—Normal.

*Color.*—New foliage: Upper side: (RHS 147A). Lower side: Green (RHS 147C). Old foliage: Upper side: Green (RHS 147A). Lower side: Green (RHS 147C).

Leaflets:

*Size.*—About 2.4 cm long×2.1 cm wide.

*Shape.*—Pointed oval.

*Base shape.*—Rounded.

*Apex shape.*—Pointed.

*Texture.*—Upper side: Leathery.

*Edge.*—Serrated.

*Serrations.*—Single.

*Petiole.*—Color: Green (RHS 146C).

*Petiole rachis.*—Color: Green (RHS 146D).

*Stipules.*—Length: 1.0 cm.

*Auricles.*—None.

*Disease resistance.*—Resistant to mildew and blackspot and average resistance to rust under normal growing conditions.

*Pest Resistance.*—Average.

*Vein color.*—Green (RHS 138B).

*Venation pattern.*—Pyramidal.

Wood:

*New wood.*—Color: Green (RHS 146D).

*Old wood.*—Color: Brown (RHS 165A).

Prickles:

*Quantity.*—Ordinary on main canes from base: Approximately 24 per 30 cm.

*Color when young.*—Brown (RHS 165B).

*Color when Mature.*—Brown (RHS 165B).

Small prickles:

*Quantity.*—On main stalks: Few. On laterals: Few.

*Color when young.*—Brown (RHS 165A).

*Color when mature.*—Brown (RHS 165A).

Winter hardiness: To Zone 7A.

I claim:

1. A new and distinct variety of groundcover rose plant, substantially as herein shown and described, characterized particularly by its resistance to black spot, resistance to powdery mildew and prolific pink-red blooms.

* * * * *

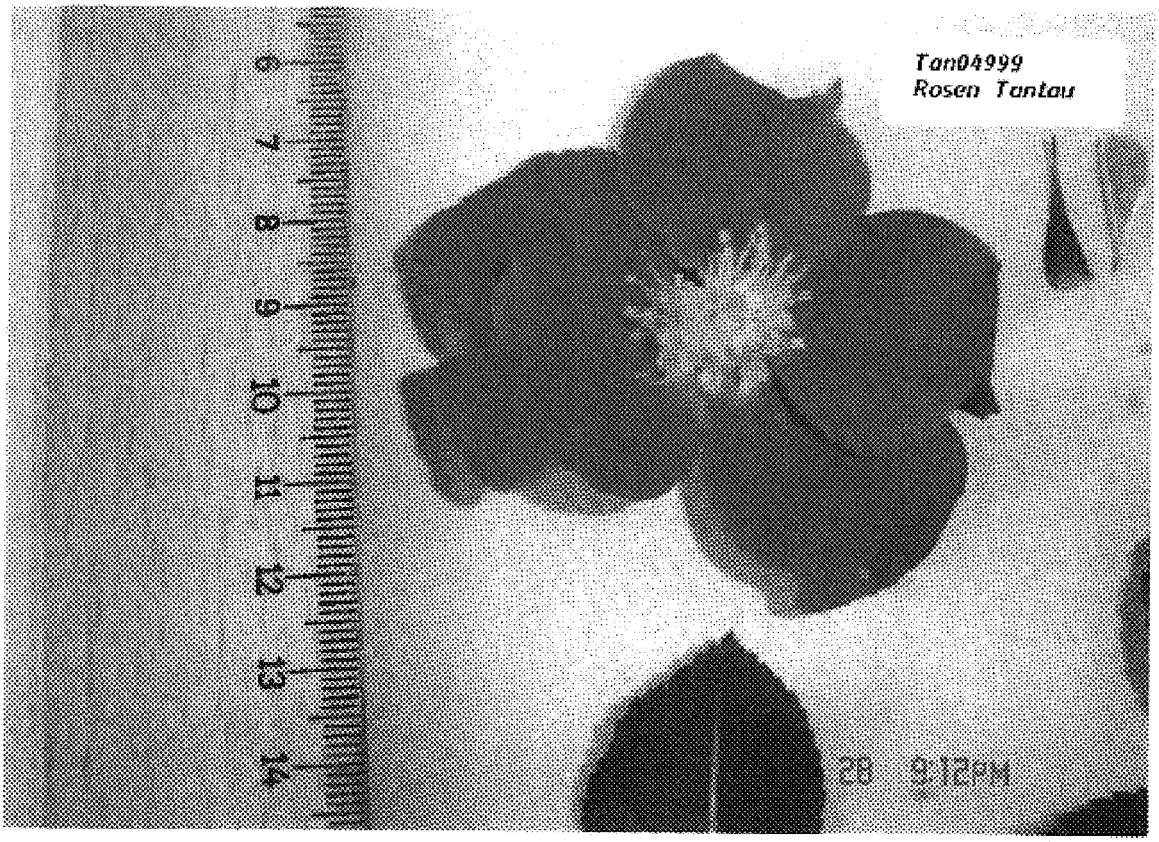
Tan04999
Rosen Tantau
28 9:12PM
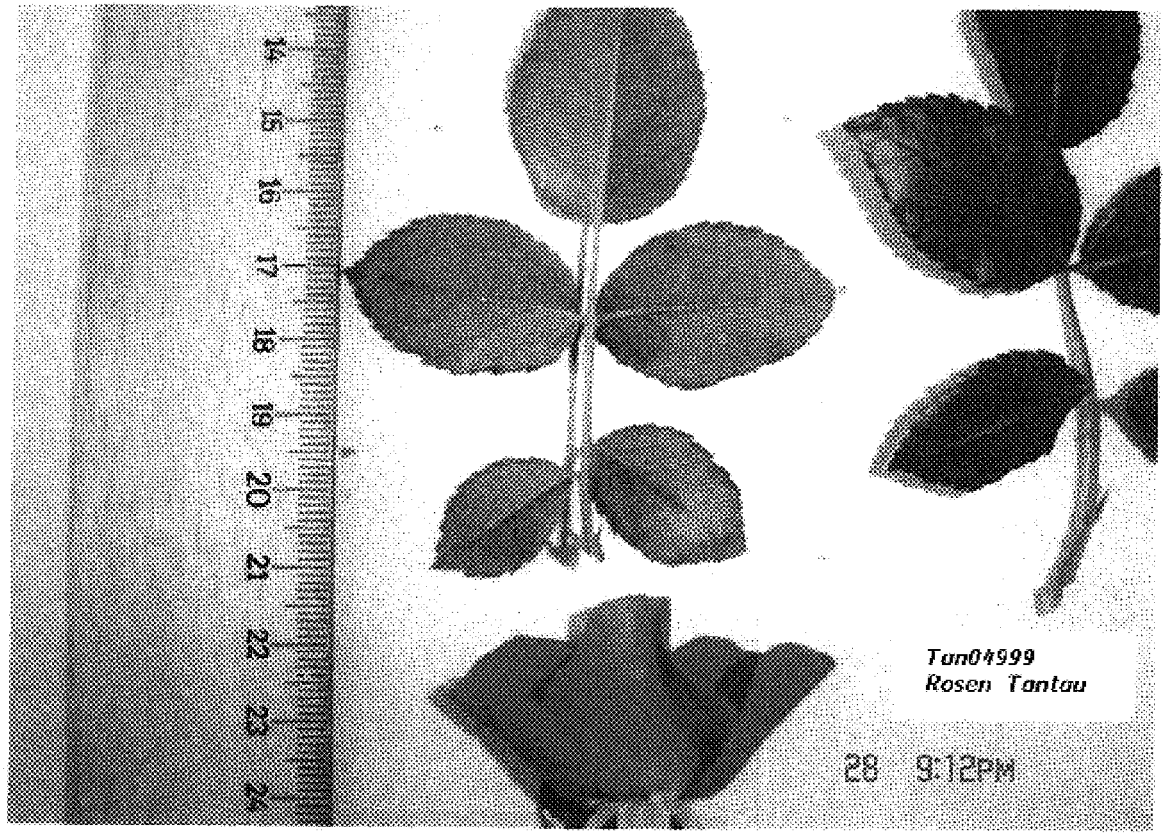
Tan04999
Rosen Tantau
28 9:12PM

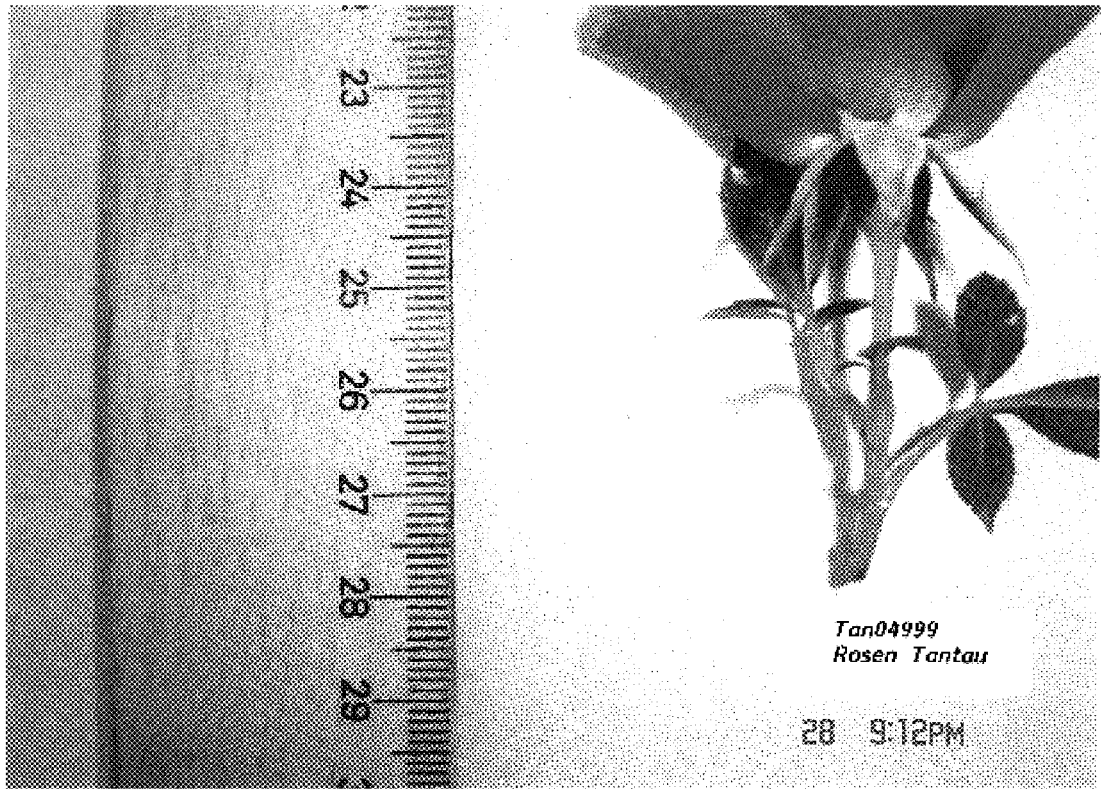
Tan04999
Rosen Tantau
28 9:12PM
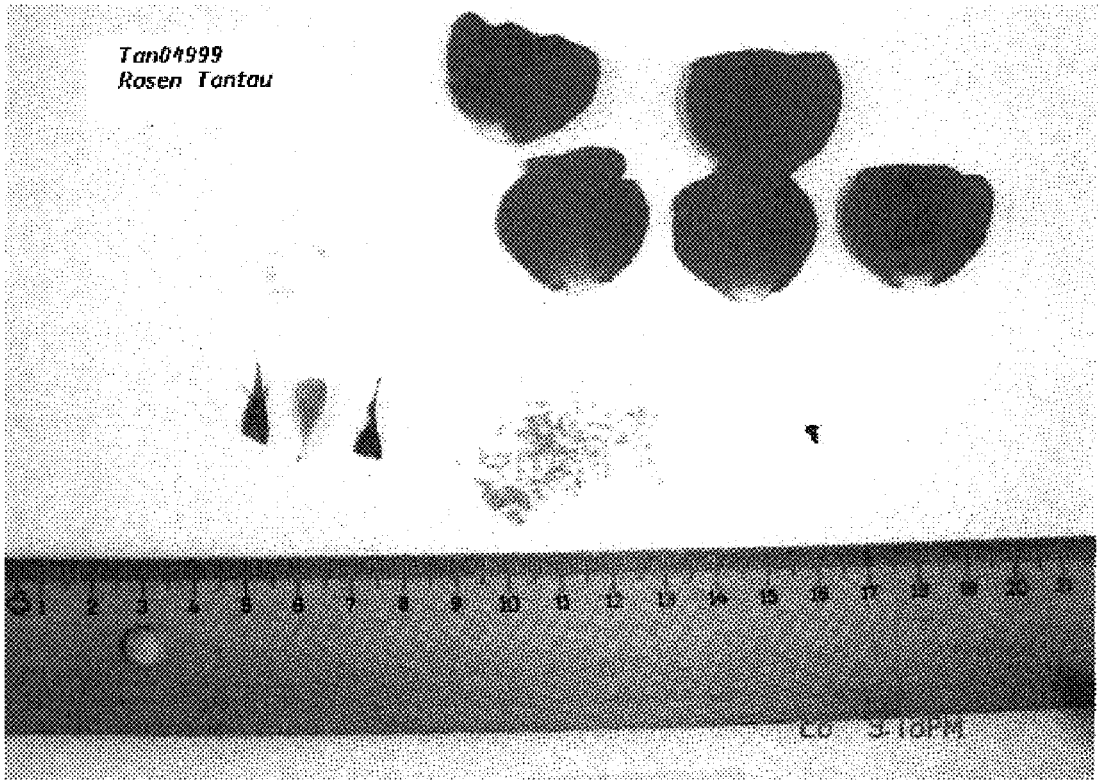
Tan04999
Rosen Tantau

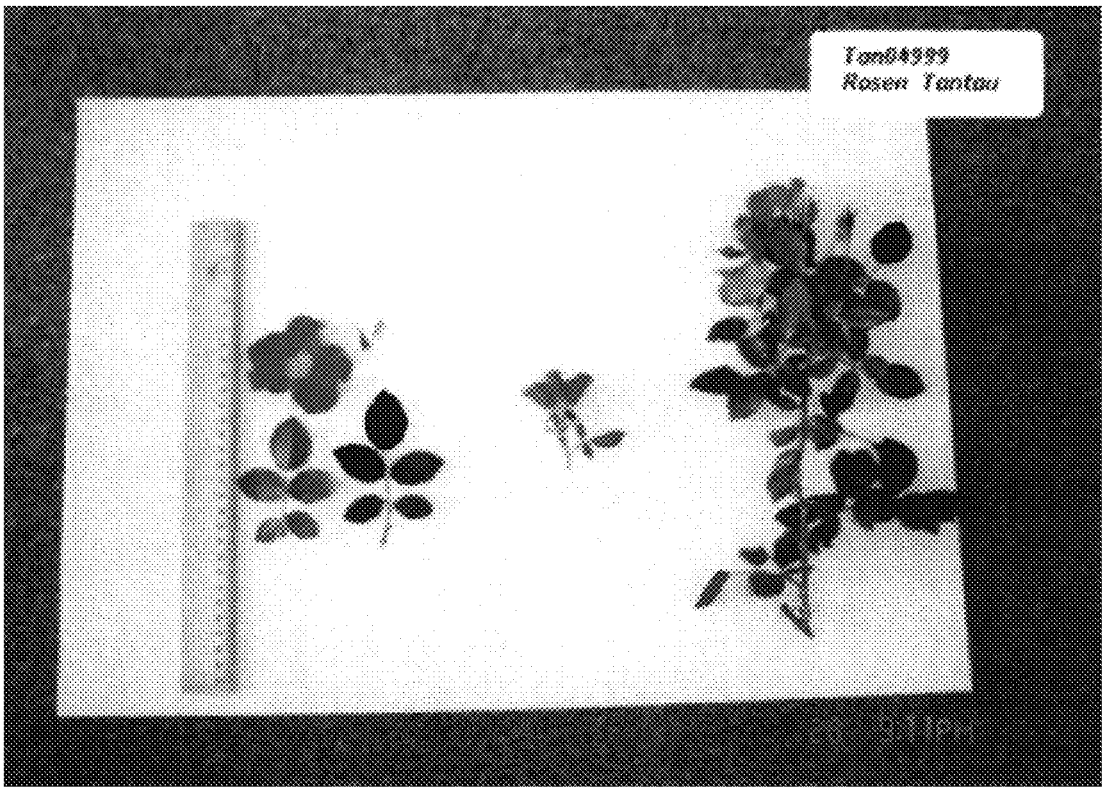
Tan04999
Rosen Tantau
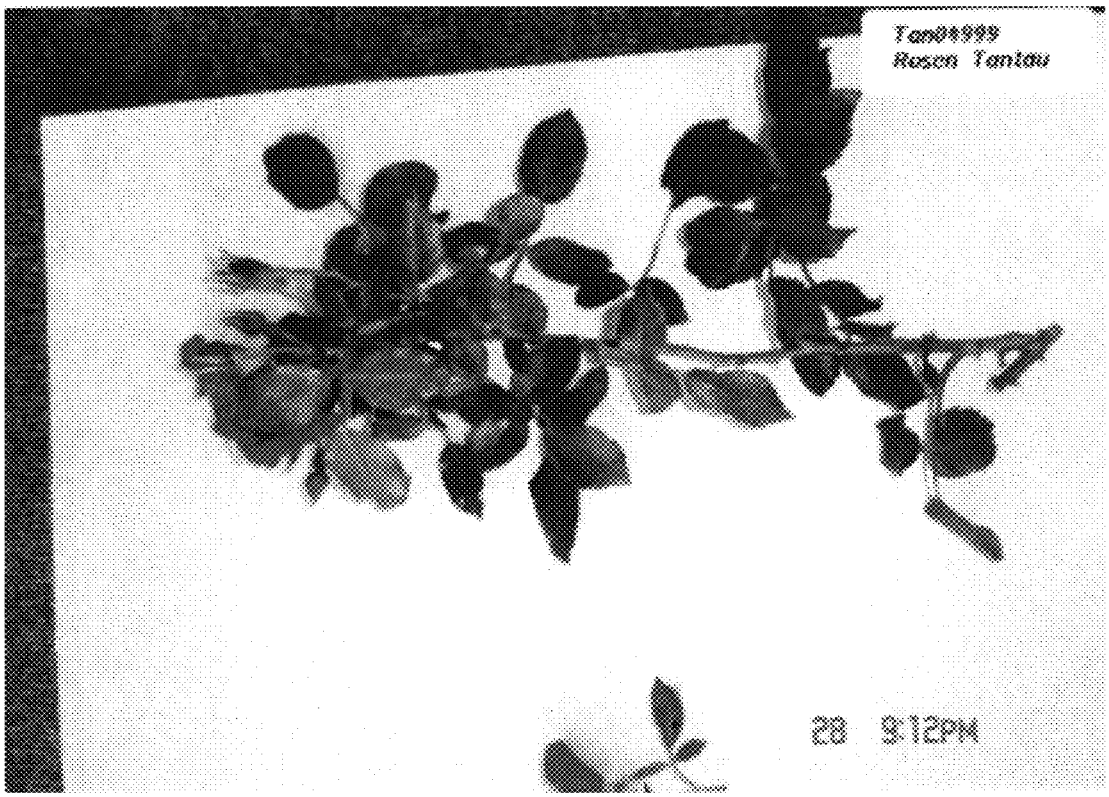
Tan04999
Rosen Tantau
28 3:12PM